(12) United States Patent
Imai

(10) Patent No.: US 10,123,709 B2
(45) Date of Patent: Nov. 13, 2018

(54) PULSE WAVE MEASUREMENT DEVICE, PULSE WAVE MEASUREMENT SYSTEM AND SIGNAL PROCESSING METHOD

(71) Applicant: KABUSHIKI KAISHA TOSHIBA, Tokyo (JP)

(72) Inventor: Shigeo Imai, Chiba Chiba (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 215 days.

(21) Appl. No.: 15/050,998

(22) Filed: Feb. 23, 2016

(65) Prior Publication Data

US 2017/0071488 A1    Mar. 16, 2017

(30) Foreign Application Priority Data

Sep. 11, 2015  (JP) .................. 2015-180029

(51) Int. Cl.
*A61B 5/02* (2006.01)
*A61B 5/024* (2006.01)
*A61B 5/00* (2006.01)
*A61B 5/11* (2006.01)

(52) U.S. Cl.
CPC .......... *A61B 5/02416* (2013.01); *A61B 5/721* (2013.01); *A61B 5/11* (2013.01); *A61B 5/7207* (2013.01); *A61B 5/7225* (2013.01); *A61B 5/7246* (2013.01); *A61B 5/7278* (2013.01); *A61B 2562/0219* (2013.01); *A61B 2562/0233* (2013.01)

(58) Field of Classification Search
CPC ....... A61B 5/02416; A61B 5/721; A61B 5/11; A61B 5/7207; A61B 5/7225; A61B 5/7246; A61B 5/7278; A61B 2562/0219; A61B 2562/0233
See application file for complete search history.

(56) References Cited

U.S. PATENT DOCUMENTS 9,113,793 B2     8/2015   Terumoto et al.
2014/0176944 A1*  6/2014   Addison ................ G01B 11/14
                                              356/400

FOREIGN PATENT DOCUMENTS

| JP | 2009005721 A | 1/2009 |
| JP | 2009291389 A | 12/2009 |
| JP | 2012143316 A | 8/2012 |
| JP | 2013162821 A | 8/2013 |

* cited by examiner

*Primary Examiner* — Amanda Hulbert
*Assistant Examiner* — Natasha Patel
(74) *Attorney, Agent, or Firm* — Patterson & Sheridan, LLP

(57) ABSTRACT

A pulse wave measurement device includes a storage unit and a subtracter. When a light emitting element alternately switches between a lighting state in which the light emitting element emits light into a body and a non-lighting state in which the light emitting element does not emit light, the storage unit stores a value of a first digital signal representing an output state of a light receiving element that receives light transmitted through or reflected by the body at timing of the lighting state, and a value of a second digital signal representing an output state of the light receiving element at timing of the non-lighting state. The subtracter subtracts the second digital signal value stored in the storage unit from the first digital signal value stored in the storage unit.

6 Claims, 5 Drawing Sheets

PULSE WAVE MEASUREMENT DEVICE, PULSE WAVE MEASUREMENT SYSTEM AND SIGNAL PROCESSING METHOD

CROSS-REFERENCE TO RELATED APPLICATION

This application is based upon and claims the benefit of priority from Japanese Patent Application No. 2015-180029, filed Sep. 11, 2015, the entire contents of which are incorporated herein by reference.

FIELD

Embodiments described herein relate to a pulse wave measurement device, a pulse wave measurement system and a signal processing method.

BACKGROUND

A method of measuring a pulse wave using an LED (Light Emitting Diode) that emits light toward a blood vessel and a photodiode that receives light transmitted through or reflected by the blood vessel is known. In this method, a signal output by a light receiving element corresponds to a pulse wave. However, this signal generally includes not just a pulse wave component but often also a low frequency noise component, such as a component due to ambient light fluctuations. Therefore, signal processing in which an HPF (High Pass Filter) is used to remove such a low frequency noise component is performed.

However, when significant low frequency noise must be removed through the HPF, it becomes necessary to perform complicated computations using lots of signal data to exclude this noise. Therefore, substantial time is spent in signal processing calculations, thus, power consumption and response time is increased as a result.

DETAILED DESCRIPTION

Example embodiments of the present disclosure provide a pulse wave measurement device, a pulse wave measurement system, and a signal processing method capable of measuring a pulse wave quickly and with low power consumption.

In general, according to one embodiment, a pulse wave measurement device (e.g., a heart/pulse rate monitoring device) includes a storage unit and a subtracter (e.g., a specialized hardware processor element or a software module operating on a more generalized processor element or elements). The storage unit is configured to store a value of a first digital signal and a value of a second digital signal. The first digital signal corresponds to an output signal level of a light receiving element configured to receive light transmitted through or reflected by a body (e.g., a human body) when a light emitting element is emitting light. The second digital signal corresponds to an output signal level of the light receiving element when the light emitting element is not emitting light. The subtracter is configured to output a correction value for the first digital signal by performing mathematical operations (e.g., subtraction and/or averaging of multiple values) using the value of the second digital signal and the value of the first digital signal.

Embodiments of the present disclosure are described below with reference to the accompanying drawings. The embodiments do not limit the present disclosure.

First Embodiment

Figure 1:
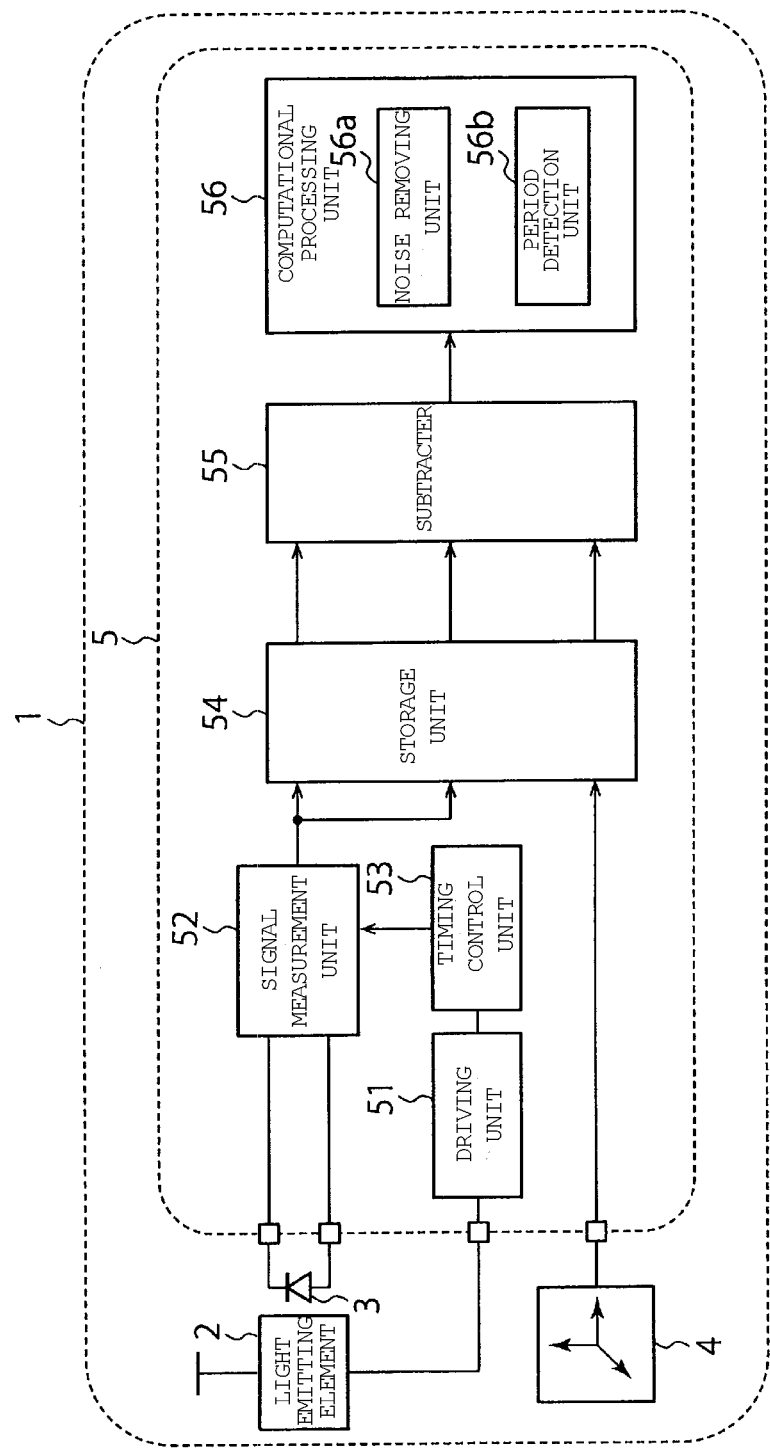
FIG. 1 is a block diagram showing a schematic configuration of a pulse wave measurement system according to a first embodiment.

FIG. 1 is a block diagram showing a schematic configuration of a pulse wave measurement system according to a first embodiment. As shown in FIG. 1, a pulse wave measurement system 1 according to the first embodiment includes a light emitting element 2, a light receiving element 3, an acceleration sensor 4 and a pulse wave measurement device 5.

The light emitting element 2 emits light into a body, specifically, toward a blood vessel of a subject person whose pulse wave is to be measured. According to the first embodiment, the light emitting device 2 includes an LED that emits green light. However, the light emitting element 2 may be other kinds of light emitting elements other than an LED, and emission color (wavelength of light) of the light emitting element 2 may also be other colors, such as red.

The light receiving element 3 receives light emitted from the light emitting element 2 which has been transmitted through or reflected by the blood vessel. The light receiving element 3 includes a photodiode, for example. However, the light receiving element 3 may be other kinds of light receiving elements other than a photodiode.

While the light emitting element 2 is emitting input light, the output state (e.g., an output signal) of the light receiving element 3 is changed in response to expansion and contraction of a blood vessel. In other words, the output state of the light receiving element 3 induced by light from the light emitting element 2 corresponds to a pulse wave in the body/blood vessel as the amount of light transmitted/reflected (and ultimately received by the light receiving element 3) changes with the expansion/contraction cycle of the pulsing blood vessel.

If the light of the light emitting element 2 is green as in the first embodiment, the light receiving element 3 receives reflected light reflected by the blood vessel. When the blood vessel is expanded, the amount of reflected light is reduced; therefore, the light receiving element 3 is put into a low output state. On the other hand, when the blood vessel is contracted, the amount of reflected light is increased; therefore, the light receiving element 3 is put into a high output state.

Note that when the light of the light emitting element 2 is, for example, red, the light receiving element 3 receives the light that is transmitted through the blood vessel. In this case (red light), since the amount of transmitted light is also reduced when the blood vessel is expanded, the light receiving element 3 is put into a low output state, and when the blood vessel is contracted, the light receiving element 3 is also put into a high output state.

The acceleration sensor 4 detects acceleration (e.g., due to movements of the body), and outputs a motion signal representing the detected acceleration to the pulse wave measurement device 5.

The pulse wave measurement device 5 includes a driving unit 51, a signal measurement unit 52, a timing controller 53, a storage unit 54, a subtracter 55 and a computational processing unit 56.

The driving unit 51 drives the light emitting element 2. Specifically, the driving unit 51 drives the light emitting element 2 based on a lighting control signal for alternately switching the light emitting element 2 between a lighting state in which the light emitting element emits light into the body and a non-lighting state in which the light emitting element does not emit light. That is, the driving unit 41 supplies power at a level corresponding to the lighting control signal which causes the light emitting element 2 to emit light or not.

The signal measurement unit 52 provides a first digital signal representing the measured output state of the light receiving element 3 at timing of the lighting state, and a second digital signal representing the measured output state of the light receiving element 3 at timing of the non-lighting state. For example, the signal measurement unit 52 includes an AFE (Analog Front End) including an A/D (Analog to Digital) converter and the like for converting an analog signal output from the light receiving element 3 into a digital signal.

The timing control unit 53 controls the timing at which the signal measurement unit 52 measures the first digital signal and the second digital signal. Specifically, the timing control unit 53 controls when signal measurement by the signal measurement unit 52 occurs so that the first digital signal is measured in synchronization with timing of the lighting state (which is based on the lighting control signal), and the second digital signal is measured in synchronization with timing of the non-lighting state (which is also based on the lighting control signal).

The storage unit 54 stores each value of the first and second digital signals measured by the signal measurement unit 52 as well as the detected value of the motion signal provided by the acceleration sensor 4.

The subtracter 55 subtracts the second digital signal value and the motion signal value stored in the storage unit 54 from the first digital signal value stored in the storage unit 54, and outputs a signal representing the subtraction result to the computational processing unit 56. In some embodiments, subtracter 55 may be implemented in dedicated hardware components which manipulate various signal values retrieved from the storage unit 54 according to at least one of the computational examples described below. In other embodiments, subtracter 55 may be implemented as a software module operating on a processor to manipulate signal values from the storage unit 54 according to at least one of the computation examples described below.

The computational processing unit 56 includes a noise removing unit 56a and a period detection unit 56b. The noise removing unit 56a removes a high frequency noise component from the signal output from the subtracter 55. For example, the noise removing unit 56a includes an LPF (Low Pass Filter) for attenuating a higher frequency signal component in a frequency band higher than a normal or expected frequency band of the pulse wave. The period detection unit 56b detects a period of the pulse wave signal which is subjected to signal processing by the noise removing unit 56a. For example, the computational processing unit 56 includes a CPU (Central Processing Unit) for performing various kinds of computational processing based on a predetermined program.

Figure 2:
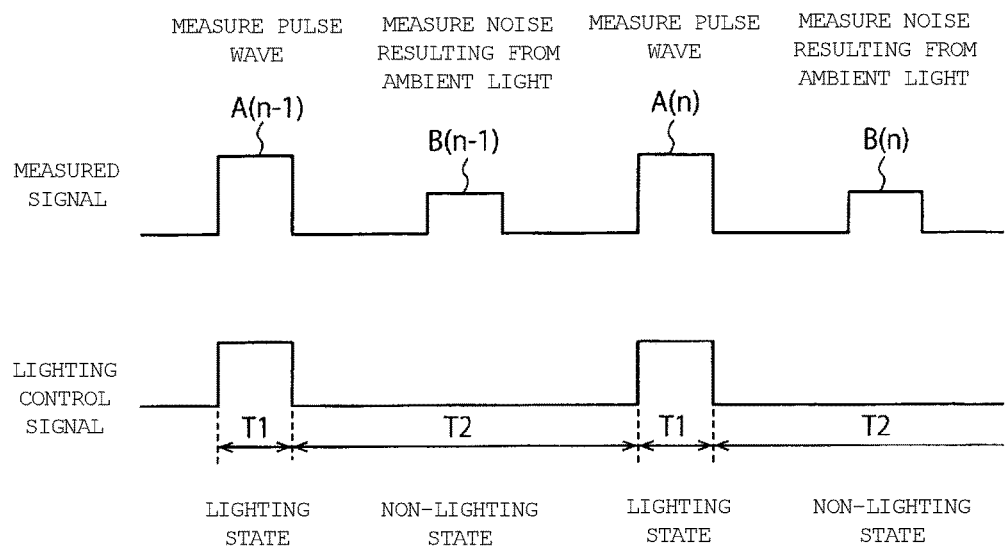
FIG. 2 is a timing chart of a signal used in the pulse wave measurement system shown in FIG. 1.

FIG. 2 is a signal timing chart depicting operation(s) in the pulse wave measurement system 1 according to the first embodiment.

First, the driving unit 51 alternately switches the light emitting element 2 between a lighting state (light on) and a non-lighting state (light off) based on the lighting control signal shown in FIG. 2. Based on the control of the timing controller 53, the signal measurement unit 52 measures a first digital signal for each timing T1 of the lighting state, and measures a second digital signal for each timing T2 of the non-lighting state. That is, the first digital signal is measured each time the light emitting element 2 is turned on, and the second digital signal is measured each time the light emitting element 2 is turned off. The second digital signal is not required to be measured continuously during the entire period of time when the light emitting element 2 is turned off. In addition, the acceleration sensor 4 detects acceleration at each timing T1, and outputs a motion signal representing the detected acceleration (not shown in FIG. 2). The first digital signal value and the second digital signal value are stored in the storage unit 54 by the signal measurement unit 52. The motion signal value is also stored in the storage unit 54.

Since the first digital signal is measured at timing T1, the first digital signal includes a pulse wave component because the first digital signal corresponds to a measured value (e.g., light intensity) that results at least in part from transmission/reflection of the emitted light by a blood vessel. However, in addition to the pulse wave component, the first digital signal also includes an ambient light-related noise component resulting from ambient or stray light, and a motion-related noise component resulting from the body motion of a subject person whose pulse wave is being measured. The ambient light-related noise component substantially corresponds to the second digital signal that is measured at timing T2 when the light emitting element 2 is in a non-lighting state (off). Meanwhile, the motion-related noise component corresponds to the motion signal detected by the acceleration sensor 4 at timing T1.

Therefore, in the first embodiment, as a result of the subtracter 55 subtracting the second digital signal value and the motion signal value from the first digital signal value, the ambient light-related noise component and the motion-related noise component are removed from the first digital signal, and a pulse wave component is extracted from the first digital signal. Note that, in the first embodiment, in order to remove the motion-related noise component with higher precision, the subtracter 55 may subtract not a raw measured value of the motion signal but rather some processed value such as the motion signal value multiplied by a coefficient K calculated by adaptation or calibration of sensor 4 output values to the body motion of the subject person whose pulse wave is measured with the motion signal value.

With reference to FIG. 2, three computational examples in which the subtracter 55 subtracts the second digital signal value from the first digital signal value can be described.

In the first computational example, the subtracter 55 subtracts, from the first digital signal value A(n) measured at timing T1, the second digital signal value B(n−1) measured at timing T2 immediately before timing T1. That is, the subtracter 55 performs a calculation of A(n)−B(n−1).

In the second computational example, the subtracter 55 subtracts the second digital signal value B(n) from the first digital signal value A(n). That is, the subtracter 55 performs calculation of A(n)−B(n) and thus uses the second digital signal (B(n)) acquired immediately after the first digital signal (A(n)).

In the third computational example, the subtracter 55 subtracts an average value of the second digital signal (B(n−1)) acquired before and the second digital signal (B(n)) acquired after the first digital signal (A(n)), that is, (B(n−1)+B(n))/2. That is, the subtracter 55 performs calculation of A(n)−(B(n−1)+B(n))/2.

After performing subtraction of one of the first to third computational examples, the subtracter 55 outputs a signal representing the subtraction result to the computational processing unit 56.

In the computational processing unit 56, the noise removing unit 56a removes a high frequency noise component included in the signal output from the subtracter 55. Then, the period detection unit 56b detects the period of the pulse wave signal subjected to signal processing by the noise removing unit 56a. Based on this period, a pulse rate is calculated.

Figure 3A:
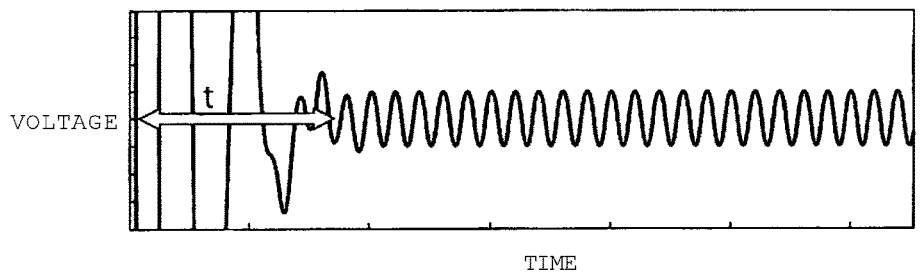
FIG. 3A is a waveform diagram of a pulse wave signal subjected to signal processing by a pulse wave measurement device according to a comparative example.
Figure 3B:
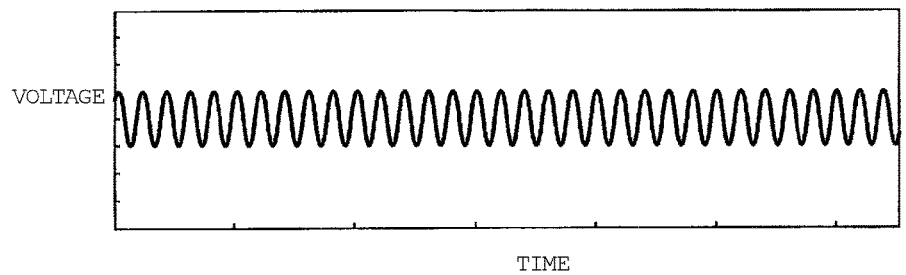
FIG. 3B is a waveform diagram of a pulse wave signal subjected to signal processing by a pulse wave measurement device according to the first embodiment.

Referring to FIGS. 3A and 3B, simulation results of the signal processing of the pulse wave measurement device 5 according to the first embodiment, and the signal processing of a pulse wave measurement device according to a comparative example are described. FIG. 3A is a waveform diagram of a pulse wave signal subjected to signal processing by a pulse wave measurement device according to a comparative example. FIG. 3B is a waveform diagram of a pulse wave signal subjected to signal processing by the pulse wave measurement device 5 according to the first embodiment.

The pulse wave measurement device according to the comparative example is different from the pulse wave measurement device 5 in that an ambient light noise component and a motion noise component are removed by using HPF rather than signal subtraction. However, when a noise component is removed by using HPF, it is necessary to perform complicated computations requiring significant amounts of signal data. Therefore, as shown in FIG. 3A, in the pulse wave measurement device according to the comparative example, in order to obtain a stable pulse wave signal, some length of signal processing time t is required before a stable signal is output.

On the other hand, the pulse wave measurement device 5 according to the first embodiment uses subtraction (by the subtracter 55) and removes the ambient light noise component and the motion noise component without using HPF processing. That is, the pulse wave measurement device 5 obtains a stable pulse wave signal by using the relatively simple computational processing of subtraction to provide a pulse wave signal value. Therefore, as shown in FIG. 3B, it is possible to quickly perform signal processing at the time of measuring a pulse wave, and to suppress power consumption of the pulse wave measurement device 5.

Second Embodiment

A pulse wave measurement system according to a second embodiment is now described. Since the pulse wave measurement system according to the second embodiment has the same configuration as that of the pulse wave measurement system 1 according to the first embodiment shown in FIG. 1, the overlapping description thereof is omitted.

Figure 4:
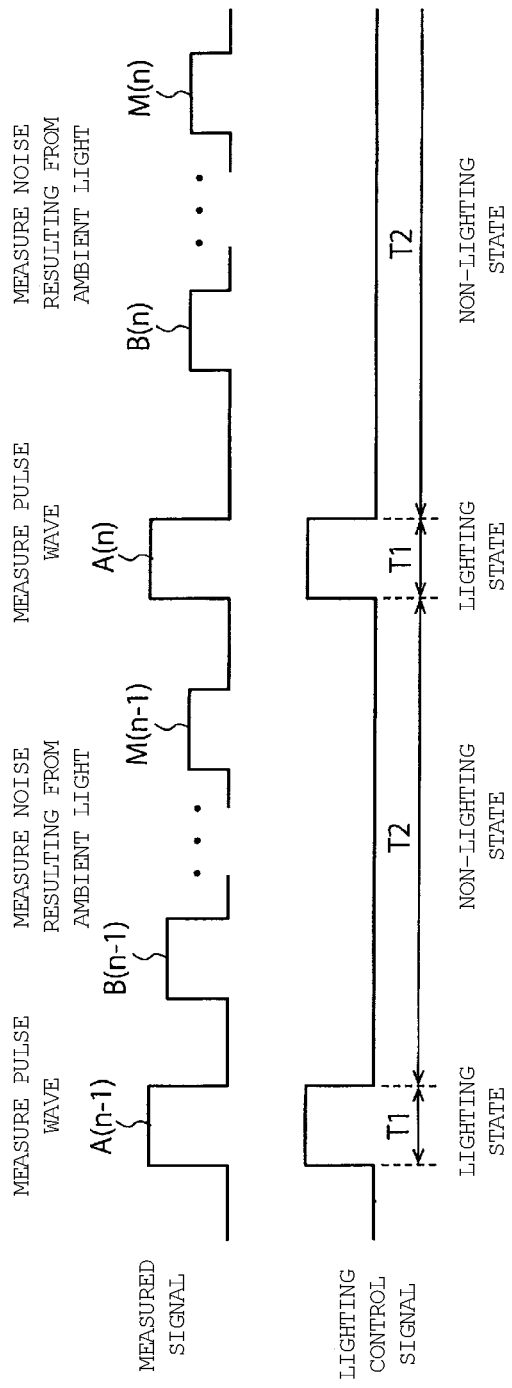
FIG. 4 is a timing chart of a signal used in a pulse wave measurement system according to a second embodiment.

The operation of the pulse wave measurement system according to the second embodiment is described below with reference to FIG. 4. FIG. 4 is a timing chart of a signal used in the pulse wave measurement system according to the second embodiment. Differences from the first embodiment described above are described below.

In the first embodiment, the signal measurement unit 52 measures a second digital signal just once during each timing T2 of the non-lighting state, In the second embodiment, as shown in FIG. 4, the signal measurement unit 52 measures a second digital signal multiple times during each timing T2 of the non-lighting state. Further, the signal measurement unit 52 calculates an average value of the second digital signal values measured at these multiple times during a non-lighting state, and stores the average value in the storage unit 54.

Then, the subtracter 55 subtracts this average value of the second digital signal values and the motion signal value from the first digital signal value. As in the first embodiment, the subtracter 55 may utilize different computational methods. Similar to in the first computational example described with respect to the first embodiment, the subtracter 55 can subtracts the average value of the second digital signal values (average of B(n−1) to M(n−1)) that were measured during the timing T2 immediately before timing T1 corresponding to the first digital signal (A(n)) from the first digital signal value A(n). Or similar to the second computational example as described with respect to in the first embodiment, the subtracter 55 may subtract the average value of the second digital signal values B(n) to M(n) measured during the timing T2 immediately after the timing T1 corresponding to the first digital signal (A(n)) from the first digital signal value A(n). Furthermore, similar to the third computational example as described with respect to in the first embodiment, the subtracter 55 may subtract an average of the average second digital signal values obtained during the timings T2 immediately before (average of B(n−1) to M(n−1)) and after (average of B(n) to M(n)) from the first digital signal value (A(n)). In other words, the subtracter 55 can subtract the mean value of the second digital signal values measured before and after timing T1 from the first digital signal value.

The operation of this second embodiment subsequent to the subtraction processing by the subtracter 55 is the same as that according to the first embodiment, and the description thereof is omitted.

According to the pulse wave measurement system according to the second embodiment described above, as in the first embodiment, simple computational processing (subtraction) of a signal value is used to remove an ambient light noise component and a motion noise component. Therefore, it is possible to quickly perform signal processing at the time of measuring a pulse wave and to reduce power consumption of the pulse wave measurement device 5.

In particular, in the pulse wave measurement system according to the second embodiment, the signal measurement unit 52 measures a second digital signal several times during timing T2 of the non-lighting state, and calculates the average value thereof. Therefore, even if a second digital signal representing a large ambient light noise component is accidentally measured once, it is possible to remove an ambient light noise component with higher precision because the second digital signal values are averaged. Note that, in the second embodiment, the computational processing of the average value of the second digital signal values is added as compared to the first embodiment. However, the computational processing of the average values is performed during timing T2 of the non-lighting state and, in general, is not complex. Thus, this processing does not prevent fast signal processing.

Third Embodiment

A pulse wave measurement system according to a third embodiment is described. Since the pulse wave measurement system according to the third embodiment has the same configuration as that of the pulse wave measurement system 1 according to the first embodiment as shown in FIG. 1, the overlapping description thereof is omitted.

Figure 5:
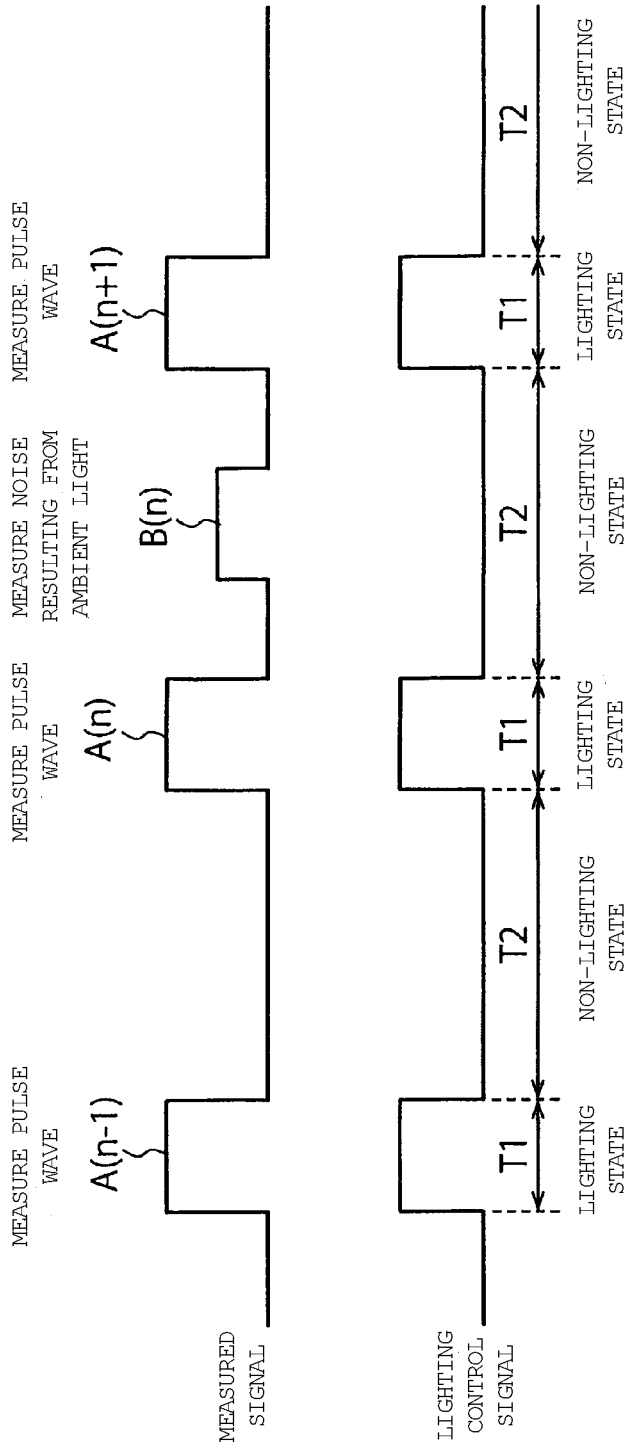
FIG. 5 is a timing chart of a signal used in a pulse wave measurement system according to a third embodiment.

The operation of the pulse wave measurement system according to the embodiment is described below with reference to FIG. 5. FIG. 5 is a timing chart of a signal in the pulse wave measurement system according to the embodiment. The differences from the first embodiment described above are described below.

In the first embodiment, the signal measurement unit 52 measures a second digital signal for each timing T2 of the non-lighting state; on the other hand, in the third embodiment, as shown in FIG. 5, the signal measurement unit 52 measures a second digital signal only at a preset timing T2 of the non-lighting state such that the second digital signal is measured during only some periods when the light emitting element 2 is off rather than during every period when the light emitting element is off. For example, the signal measurement unit 52 measures a second digital signal at a rate of once every two timings T2. That is, the second digital signal is acquired only during every other timing T2 rather than during every timing T2.

Then, the subtracter 55 subtracts the second digital signal value and the motion signal value from the first digital signal value. At this time, the subtracter 55 subtracts the second digital signal value measured at timing T2 as close as possible to timing T1 corresponding to the first digital signal, thus, it is possible to remove an ambient light noise component with high precision.

The operation subsequent to the subtraction by the subtracter 55 described above is the same as that according to the first embodiment, and the description thereof is omitted.

According to the pulse wave measurement system of the third embodiment described above, as in the first embodiment, simple computational processing (subtraction) of a signal value is used to remove an ambient light noise component and a motion noise component. Therefore, it is possible to quickly perform signal processing at the time of measuring a pulse wave, thus, it is possible to reduce power consumption of the pulse wave measurement device 5.

In particular, in the pulse wave measurement system according to the third embodiment, the number of measurements of the second digital signal is reduced in comparison with that according to the first embodiment. Therefore, since the load of signal processing is reduced, it is possible to further reduce the power consumption of the pulse wave measurement device 5. The pulse wave measurement system according to the third embodiment is particularly suitable for the case where a pulse wave is measured in an environment where the amplitude changes in the second digital signal values, in other words, the variations in the ambient light noise components is small.

Fourth Embodiment

A pulse wave measurement system according to a fourth embodiment is described. Here, components similar to those of the pulse wave measurement system 1 according to the first embodiment described above are denoted by the same reference numerals, and detailed description thereof is omitted.

Figure 6:
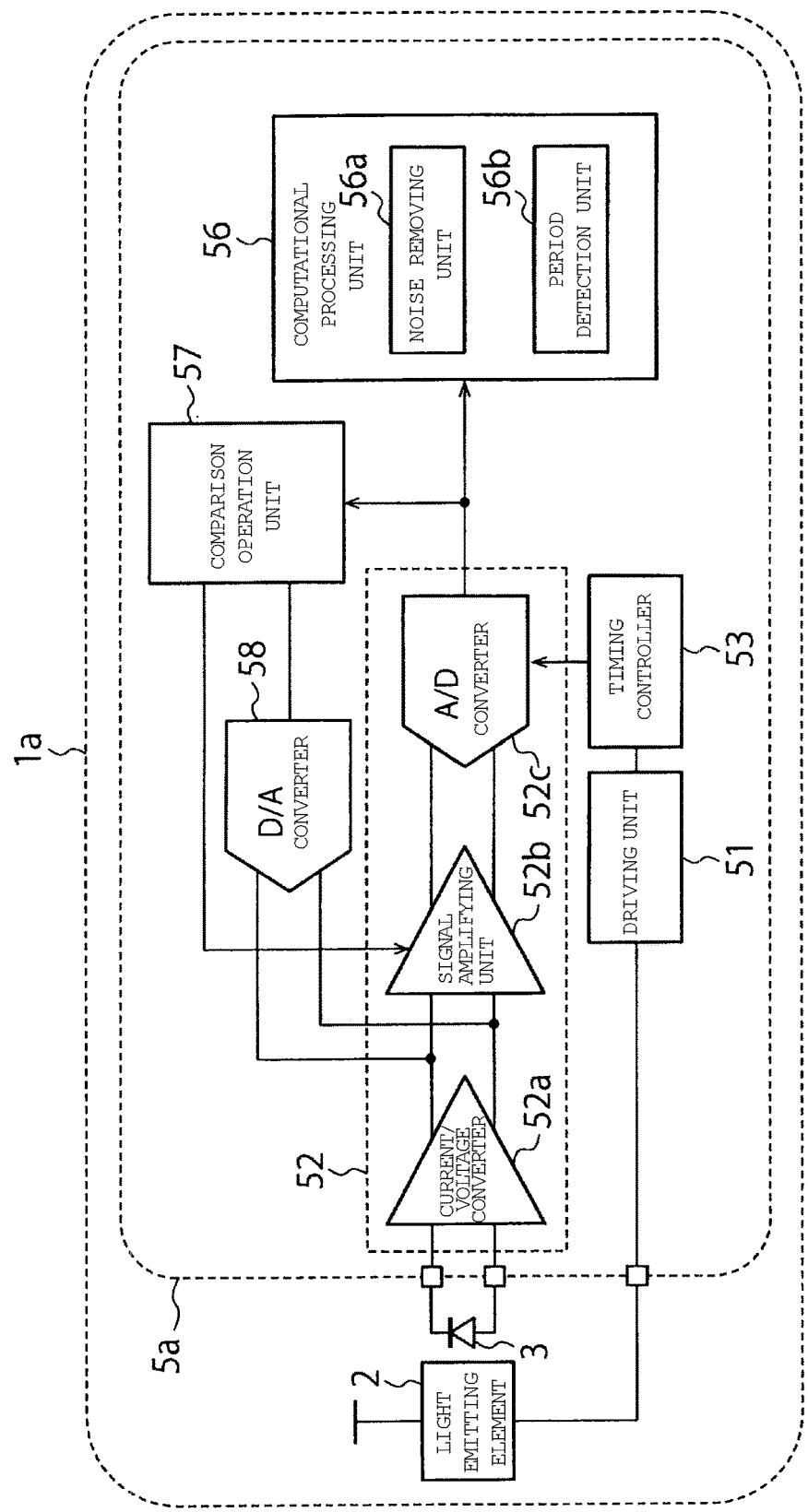
FIG. 6 is a block diagram showing a schematic configuration of a pulse wave measurement system according to a fourth embodiment.

FIG. 6 is a block diagram showing a schematic configuration of a pulse wave measurement system according to the fourth embodiment. As shown in FIG. 6, a pulse wave measurement system 1a according to the fourth embodiment includes a light emitting element 2, a light receiving element 3 and a pulse wave measurement device 5a. The pulse wave measurement device 5a includes the driving unit 51, the signal measurement unit 52, the timing controller 53, the computational processing unit 56, a comparison operation unit 57 and a D/A converter 58. Since the driving unit 51 and the timing control unit 53 are substantially the same components as those of the first embodiment, the details of the signal measurement unit 52, the comparison operation unit 57 and the D/A converter 58 will be described.

The signal measurement unit 52 includes a current/voltage converter 52a, a signal amplifying unit 52b and an A/D converter 52c. The current/voltage converter 52a converts a current signal output from the light receiving element 4 into an analog voltage signal The analog voltage signal corresponds to a first analog signal when the light emitting element 2 is in a lighting state (on), and corresponds to a second analog voltage signal when the light emitting element 2 is in a non-lighting state (off). The signal amplifying unit 52b amplifies the first analog voltage signal and the second analog voltage signal. The amplification value of the signal amplifying unit 52b is variable. The A/D converter 52c converts each analog voltage signal amplified by the signal amplifying unit 52b into a digital signal. The digital signal corresponds to a first digital signal when the light emitting element 2 is in a lighting state (on), and corresponds to a second digital signal when the light emitting element 2 is in a non-lighting state (off).

The comparison operation unit 57 performs a comparison operation between the second digital signal value and a preset reference value. The preset reference value may be about half of a full scale or expected signal, for example. In addition, in accordance with the comparison operation result, the comparison operation unit 57 generates an offset digital value having polarity that is opposite to the second digital signal value.

The D/A converter 58 converts the offset digital value generated by the comparison operation unit 57 into an analog value, and adds the converted analog value to the first analog signal.

The operation of the pulse wave measurement system 1a according to the fourth embodiment is now described focusing on operation different from that according to the first embodiment described above.

First, the signal amplifying unit 52b amplifies a second analog signal output from the current/voltage converter 52a with a preset amplification value. Then, the A/D converter 52c converts the amplified second analog signal into a second digital signal and outputs the second signal to the comparison operation unit 57.

The comparison operation unit 57 performs comparison operation between the second digital signal value and a preset reference value. If the second digital signal value is lower than the preset reference value, the comparison operation unit instructs the signal amplifying unit 52b to perform amplification with an amplification value greater than a preset amplification value. Based on this instruction, the signal amplifying unit 52b amplifies the second analog signal with an amplification value greater than the preset amplification value, again. Then, the comparison operation unit 57 performs comparison operation between the second digital signal value and the preset reference value.

As a result, if the second digital signal value is greater than the preset reference value, the comparison operation unit 57 generates an offset digital value having polarity opposite thereto and outputs the digital value to the D/A converter 58. On the other hand, if the second digital signal value is lower than the preset reference value, the signal amplifying unit 52b performs amplification of the second analog signal with a greater amplification value. That is, the comparison operation unit 57 adjusts the amplification value of the signal amplifying unit 52b so that the second digital signal value becomes larger than the preset reference value.

Based on the offset digital value generated by the comparison operation unit 57, the D/A converter 58 performs analog signal processing of the first analog signal. Thus, an ambient light noise component is removed from the first analog signal. Finally, based on the amplification value derived by the comparison operation unit 57, the signal amplifying unit 52b amplifies a first analog signal from which the ambient light noise component has been removed.

In the pulse wave measurement system 1a according to the fourth embodiment described above, the second analog signal corresponding to the ambient light noise component is first amplified with a preset amplification value. Then, comparison operation is performed between the second digital signal value and the preset reference value.

At this time, the amplification value of the signal amplifying unit 52b is adjusted so that the second digital signal value becomes larger than the preset reference value. Then, an offset digital value having polarity opposite to the second digital signal value is generated based on the adjusted amplification value, and the first analog signal is subjected to analog signal processing based on the offset digital value. Thus, an offset canceling operation for removing an ambient light noise component from the first analog signal is performed.

After the offset canceling operation, the first analog signal is amplified as much as possible within limits such that no signal clipping occur, thus, it is still possible to measure a pulse wave signal component with high precision. Note that each analog signal may be amplified with a preset certain amplification value without adjustment of the amplification value of the signal amplifying unit 52b when there is little change in an ambient light noise component.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed:

1. A signal processing method, comprising:
   amplifying a first analog signal corresponding to an output state of a light receiving element measured when a light emitting element is emitting light, the light receiving element being configured to receive light transmitted through or reflected by a body;
   converting the amplified first analog signal into a first digital signal;
   storing a value of the first digital signal;
   amplifying a second analog signal corresponding to the output state of the light receiving element measured when the light emitting element is not emitting light;
   converting the amplified second analog signal into a second digital signal;
   storing a value of the second digital signal;
   generating an offset digital signal based on the second digital signal, the offset digital signal having a polarity opposite to the second digital signal;
   converting an offset digital value to an offset analog value; and
   processing the first analog signal by adding the first analog signal to the offset analog value.

2. The signal processing method according to claim 1, further comprising:
   subtracting the value of the second digital signal from the value of the first digital signal.

3. The signal processing method according to claim 1, wherein generating the offset digital value includes:
   performing comparison operation between the value of the second digital signal and a preset reference value,
   adjusting an amplification value to generate an adjusted second digital signal having a value larger than the preset reference value, and
   outputting the offset digital value based on the adjusted second digital signal.

4. The signal processing method according to claim 3, further comprising:
   amplifying the processed first analog signal.

5. The signal processing method according to claim 3, further comprising:
   amplifying the processed first analog signal by a factor equal to the adjusted amplification value.

6. The signal processing method according to claim 2, further comprising:
   subtracting a value of a motion signal corresponding to acceleration of the body detected by an acceleration sensor from the value of the first digital signal.

* * * * *